(12) United States Patent
Mukunda et al.

(10) Patent No.: US 10,596,159 B2
(45) Date of Patent: Mar. 24, 2020

(54) METHOD AND COMPOSITION FOR TREATING CACHEXIA AND EATING DISORDERS

(71) Applicant: India Globalization Capital, Inc., Bethesda, MD (US)

(72) Inventors: Ramachandra Mukunda, Potomac, MD (US); Ranga Chelva Krishna, Englewood, NJ (US)

(73) Assignee: India Globalization Capital, Inc., Bethesda, MD (US)

( * ) Notice: Subject to any disclaimer, the term of this patent is extended or adjusted under 35 U.S.C. 154(b) by 0 days.

(21) Appl. No.: 15/751,901

(22) PCT Filed: Aug. 11, 2016

(86) PCT No.: PCT/US2016/046451
§ 371 (c)(1),
(2) Date: Feb. 12, 2018

(87) PCT Pub. No.: WO2017/027651
PCT Pub. Date: Feb. 16, 2017

(65) Prior Publication Data
US 2018/0228788 A1   Aug. 16, 2018

Related U.S. Application Data

(60) Provisional application No. 62/203,968, filed on Aug. 12, 2015.

(51) Int. Cl.
| *A61K 31/445* | (2006.01) |
| *A61K 31/05* | (2006.01) |
| *A61K 31/352* | (2006.01) |
| *A61K 36/185* | (2006.01) |
| *A61K 31/4418* | (2006.01) |
| *A61P 43/00* | (2006.01) |
| *A61P 3/04* | (2006.01) |

(52) U.S. Cl.
CPC ............ *A61K 31/445* (2013.01); *A61K 31/05* (2013.01); *A61K 31/352* (2013.01); *A61K 31/4418* (2013.01); *A61K 36/185* (2013.01); *A61P 3/04* (2018.01); *A61P 43/00* (2018.01)

(58) Field of Classification Search
CPC .................................................. A61K 31/445
See application file for complete search history.

(56) References Cited

U.S. PATENT DOCUMENTS

| 5,240,937 | A | 8/1993 | Kelley |
| 5,391,740 | A | 2/1995 | Wang et al. |
| 6,503,532 | B1 | 1/2003 | Murty |
| 6,683,086 | B2 | 1/2004 | Druzgala et al. |
| 6,949,582 | B1 | 9/2005 | Wallace |
| 8,859,540 | B2 | 10/2014 | Rundfeldt et al. |
| 10,117,891 | B2 | 11/2018 | Mukunda et al. |
| 2004/0043043 | A1 | 3/2004 | Schlyter et al. |
| 2004/0138293 | A1 | 7/2004 | Werner et al. |
| 2005/0042172 | A1 | 2/2005 | Whittle |
| 2006/0127499 | A1 | 6/2006 | Lazarev et al. |
| 2006/0257502 | A1 | 11/2006 | Liu |
| 2007/0293440 | A1 | 12/2007 | Smith-Swintosky et al. |
| 2007/0293476 | A1 | 12/2007 | Smith-Swintosky et al. |
| 2008/0254017 | A1 | 10/2008 | Kane et al. |
| 2010/0035978 | A1 | 2/2010 | Guy et al. |
| 2011/0065627 | A1 | 3/2011 | Barathur |
| 2011/0217278 | A1 | 9/2011 | Felder |
| 2011/0301238 | A1 | 12/2011 | Borges |
| 2012/0004251 | A1 | 1/2012 | Whalley et al. |
| 2012/0165402 | A1 | 6/2012 | Whalley et al. |
| 2012/0322782 | A1 | 12/2012 | Narishetty et al. |
| 2013/0065898 | A1 | 3/2013 | Rundfeldt et al. |
| 2013/0296398 | A1 | 11/2013 | Whalley et al. |
| 2013/0309306 | A1 | 11/2013 | Rogawski et al. |
| 2014/0050789 | A1 | 2/2014 | Bogawski et al. |
| 2014/0155456 | A9 | 6/2014 | Whalley et al. |
| 2014/0243405 | A1 | 8/2014 | Whalley et al. |
| 2014/0348926 | A1 | 11/2014 | Hoffman et al. |
| 2015/0086494 | A1 | 3/2015 | Sekura et al. |
| 2015/0265637 | A1 | 9/2015 | Kane et al. |
| 2015/0359756 | A1 | 12/2015 | Guy et al. |
| 2017/0027978 | A1 | 2/2017 | Mukunda et al. |
| 2018/0161285 | A1 | 6/2018 | Mukunda et al. |

FOREIGN PATENT DOCUMENTS

| CA | 2424356 A | 4/2003 |
| WO | WO 2001/00196 A2 | 1/2001 |
| WO | WO 02/064109 A2 | 8/2002 |
| WO | WO 2004/075896 A1 | 9/2004 |
| WO | WO 2010/048423 A1 | 4/2010 |
| WO | WO 2011/063164 A2 | 5/2011 |

(Continued)

OTHER PUBLICATIONS

Kardinal et al., Cancer, Jun. 12, 1990, pp. 2657-2662.*

(Continued)

*Primary Examiner* — Paul V Ward

(74) *Attorney, Agent, or Firm* — Studebaker & Brackett PC

(57) ABSTRACT

The invention provides treating cachexia and eating disorders in humans and veterinary animals by administering a composition including: (i) cyproheptadine (CYP); and (ii) a cannabis compound selected from the group of cannabidiol (CBD) and mixtures of CBD and up to 50% tetrahydrocannabinol (THC).

18 Claims, No Drawings

(56) References Cited

FOREIGN PATENT DOCUMENTS

| WO | WO 2011/110866 A1 | 9/2011 | |
|----|----|----|----|
| WO | WO2014/145490 * | 9/2014 | ............... A01H 5/00 |
| WO | WO 2014/145490 A2 | 9/2014 | |
| WO | WO 2016/044370 A1 | 3/2016 | |
| WO | WO 2016/059399 A1 | 4/2016 | |
| WO | WO 2016/118391 A1 | 7/2016 | |
| WO | WO 2016/160542 A1 | 10/2016 | |
| WO | WO 2017/027651 A1 | 2/2017 | |
| WO | WO 2017/218629 A1 | 12/2017 | |
| WO | WO 2018/160510 A1 | 9/2018 | |

OTHER PUBLICATIONS

U.S. Appl. No. 15/104,556, filed Jun. 15, 2016 (pending).
International Application S.N. PCT/US2017/037394, filed Jun. 14, 2017 (pending).
PCT Search Report dated Dec. 10, 2015, in International App. S.N. PCT/US2015/050342, filed Sep. 16, 2015 (9 pages).
PCT Search Report dated Mar. 16, 2016, in International App. S.N. PCT/US2016/013323, filed Jan. 14, 2016 (8 pages).
PCT Search Report dated Jun. 17, 2016, in International App. S.N. PCT/US2016/24145, filed Mar. 25, 2016 (10 pages).
PCT Search Report dated Oct. 31, 2016, in International App. S.N. PCT/US2016/46451, filed Aug. 11, 2016 (9 pages).
PCT Search Report dated Aug. 31, 2017, in International App. S.N. PCT/US2017/037394, filed Jun. 14, 2017 (10 pages).
Siemens et al., Effect of cannabis on pentobarbital-induced sleeping time and pentobarbital metabolism in the rat, Biochemical Pharmacology, vol. 23: 477-488, 1974 [retrieved on Feb. 25, 2016]. Retrieved from the internet :<URL: http://www.sciencedirect.com/science/article/pii/0006295274906121>abstract.
Schlanger, S et al., Diet Enriched with Omega-3 Fatty Acids Alleviates Convulsion Symptoms in Epilepsy Patients. Epilepsia. 2002. vol. 43. No. 1; abstract; p. 103, first-second columns; p. 104, first column.
McMahan, K. Hemp Seed Oil—Why Should We Use It 48 Monterey Bay Hollistic Alliance. 2014; https://montereybayhollistic.wordpress.com/2014/08/23/hemp-seed-oil/; pp. 1-2, 4.
Kardinal. CG et al. Controlled trial of cyproheptadine in cancer patients with anorexia and/or cachexia. Cancer. Jun. 15, 1990. vol. 65. pp. 2657-2662; abstract; p. 2659. left column, 2nd, 4th paragraphs; p. 2661, right column, 2nd paragraph; table 5.
U.S. Appl. No. 16/148,775, filed Oct. 1, 2018 (pending).
Office Action dated May 15, 2018 in U.S. Appl. No. 15/104,556, filed Jun. 16, 2016 (pending).
Leo, Lowe (Potentiation of Ethanol-Induced Hepatic Vitamin A Depletion by Phenobarbital and Butylated Hydroxytoluene, Jan. 1987, Abstract Only).
Okusaka (Phase I and pharmacokinetic clinical trial of oral administration of the acyclic retinoid NIK-333, Apr. 2011, Abstract only).
International Application S.N. PCT/US2018/019814, filed Feb. 27, 2018 (pending).
PCT Search Report dated Apr. 20, 2018 in International App. S.N. PCT/US2018/019814, filed Feb. 27, 2018 (11 pages).

* cited by examiner

METHOD AND COMPOSITION FOR TREATING CACHEXIA AND EATING DISORDERS

CROSS-REFERENCE TO RELATED APPLICATIONS

The present application claims priority on prior U.S. Provisional Application Ser. No. 62/203,968, filed Aug. 12, 2015, which is hereby incorporated herein in its entirety by reference.

FIELD AND BACKGROUND OF THE INVENTION

This invention relates to methods and compositions containing cyproheptadine and cannabidiol (CBD) for treating cachexia and eating disorders in humans and veterinary animals.

About 1.3 million humans in the United States are affected each year by cachexia which is a weakness and wasting away of the body due to severe illness such as cancer, multiple sclerosis, Parkinson's disease, HIV/AIDS and other progressive illnesses. Cachexia is secondary to an underlying disease such as cancer or AIDS and is a positive risk factor for death. It is often seen at the end-stage of cancer. (Payne, et al. 2012; Rapini et al. 2007).

Cancer induced cachexia is responsible for about 20% of all cancer deaths. It physically weakens patients to the extent that response to standard treatments is poor. (Lainscak, et al. 2007; Bossola, et al. 2007).

Studies have shown that non-drug therapies such as nutritional counseling, psychotherapeutic interventions, and physical training can be an effective treatment for cachexia. Treatments involving a combination of nutrition, medication and non-drug treatment have been more effective than mono-therapy. These studies suggest that cannabinoids not be used to treat cachexia due to a lack of conclusive evidence of efficacy or safety. (European Palliative Care Research Collaborative. New European Guidelines: epcr-c.org/guidelines.php?p=cachexia).

Suzuki, et al. report that cyproheptadine was effective in stimulating appetite but had only slight effects on weight loss. (Suzuki, et al. 2013).

Ronga, et al. report that cyproheptadine only mildly stimulated appetite in advanced cancer patients but did not prevent progressive weight loss. (Ronga, et al. 2014).

The appetite-stimulating effect of cannabis has been reported in anecdotal cases. (Gorter, 1999; Felder, et al. 1998; Mikuriya, et al. 1969; Aquino, et al. 2005; Kirkham, et al. 2001).

Delta-9-tetrahydrocannabinol (THC), a constituent of cannabis, has been used as an anti-emetic drug in cancer patients receiving chemotherapy. THC has also shown stimulation of appetite and increase of body weight in HIV-positive and cancer patients. (Gorter, 1999). Another study looked at the impact of combining CYP and cannabis compounds on seizures in mice. (Ghosh, et al. 1978).

SUMMARY OF THE INVENTION

The invention provides methods and compositions for treating cachexia and eating disorders in humans and veterinary animals by administering to a subject in need thereof a composition including: (i) cyproheptadine (CYP); and (ii) a cannabis compound selected from the group of cannabidiol (CBD) and mixtures of CBD and up to 50% tetrahydrocannabinol (THC).

The CBD and THC components can be synthetic (chemically synthesized) or phytocannabinoids compounded from Cannabis plants such as sativa, indicia or hemp.

A preferred source of CBD is so-called organic CBD which is solvent compounded CBD containing minor or trace amounts of THC, cannabinol (CBN), cannabichromene (CBC), cannabigerol (CBG), terpenoids and flavonoids.

The preferred maximum dosage of CYP is about 0.2 mg/day for each kg of patient body weight and the minimum dosage of CBD is about 10 mg/day for each kg of patient body weight up to a maximum of about 300 mg/day. The invention allows for the use of low amounts of CYP with greater amounts of cannabis compound, for example in the ratio of about 1:50 up to about 1:1500.

DETAILED DESCRIPTION OF THE PREFERRED EMBODIMENT(S) OF THE INVENTION

Cyproheptadine is 4-(5H-dibenzo [a,d]cyclohepten-5-ylidene)-1-methylpiperidine hydrochloride. It is sold as Periactin or Peritol.

Cyproheptadine is a $H_1$-antihistamine with other tricyclics and tetracyclics including, promethazine, alimemazine (trimeprazine), azatadine, and ketotifen. However, unlike other antihistamines, cyproheptadine does not prevent the release of histamine; rather it competes with free histamine for binding at HA-receptor sites, thus antagonizing the effects of histamine on the HA-receptor sites, leading to a reduction in negative effects of histamine HA-receptor binding. Cyproheptadine competitively antagonizes the effects of histamine on HA-receptors in the GI tract, and large blood vessel that can lead to appetite stimulation.

The blockage of central muscarinic receptors is believed to account for cyproheptadine's antiemetic effects, although the exact mechanism is unknown. Cyproheptadine also competes with serotonin at the 5-HT2 receptor sites in the smooth muscle in the intestines and other locations. Antagonism of serotonin on the appetite center of the hypothalamus may account for cyproheptadine's ability to stimulate appetite.

The combination of CYP and cannabis is believed to work on two different pathways in controlling cachexia and eating disorders by increasing the desirability of food and increasing appetite.

The combination of lower dose CYP with cannabis compounds unexpectedly leads to: i) a reduction of side effects, such as aggressive behavior and excitement otherwise present when CYP is used alone; and ii) increased appetite over using CBD, THC, cannabis or cannabis compounds alone.

Cannabis compounds comprise tetrahydrocannabinol "THC" (9-Tetrahydrocannabinol (delta-9 THC), 8-tetrahydrocannabinol (Delta-8 THC) and 9-THC Acid) and cannabidiol (CBD). Solvent compounded CBD, so-called organic CBD, contains lesser or trace amounts of THC, cannabinol (CBN), cannabichromene (CBC), cannabigerol (CBG), terpenoids and flavonoids. Synthetic or pure CBD is free of THC and other compounds and comprises a cannabis compound for purposes of this specification.

THC and CBD can be extracted from a cannabis indica dominant strain using, for example, high pressure and carbon dioxide as a solvent in a 1500-20 L subcritical/supercritical $CO_2$ system made by Apeks Super Critical Systems, 14381 Blamer Rd., Johnstown, Ohio, 43031. (apekssupercritical.com/botanical-extraction-systems/).

Super-critical and sub-critical processors including Apeks Systems employ valveless expansion technology with no constrictions or regulating valves to cause clogging in the system between the treatment vessel and the $CO_2$ expansion separator. Flow of liquid $CO_2$ and dissolved oil travels from the treatment vessel into the separator, and the oil is separated from the $CO_2$ in the separator/collection vessel. $CO_2$ is recycled during the process and recovered and regenerative heat capture methods are used to increase efficiency.

The preferred maximum dosage of CYP is about 0.2 mg/day for each kg of patient body weight and the minimum dosage of the cannabis compound is about 10 mg/day for each kg of patient body weight up to a maximum of about 300 mg/day. The invention allows for the use of low amounts of CYP with greater amounts of cannabis compound, for example in the ratio of about 1:50 up to about 1:1500. The combination can be administered orally with food for 30 days.

EXAMPLE

Three dogs 10-12 years old had no known chronic diseases but each had all lost 10-15% of their body weight over the preceding 12 months. A combination of 0.25 mg/kg body weight/day of cyproheptadine along with 10 mg/kg body weight/day of CBD oil was administered with food for 30 days. All three dogs gained back 50% of the weight lost and all three dogs finished their food. No side effects such as excitability or aggressive behavior were observed. In humans, the dosage of CYP can be reduced to 0.2 mg/kg body weight/day for 90 days with patients experiencing reduced side effects and increased appetite.

Those skilled in the art will recognize, or be able to ascertain many equivalents to the specific embodiments of the invention described herein.

While this invention has been described as having preferred sequences, ranges, ratios, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

REFERENCES

1. Payne, C., P. J. Wiffen, and S. Martin. "Interventions for fatigue and weight loss in adults with advanced progressive illness." The Cochrane Library (2012).
2. Rapini, R. P., Bolognia, J. L., Jorizzo, J. L. Dermatology: 2-Volume Set. St. Louis: Mosby (2007): 1169.
3. Lainscak, M. Podbregar, M., Anker, S. D. "How does cachexia influence survival in cancer, heart failure and other chronic diseases?". Current Opinion in Supportive and Palliative Care 1.4 (2007): 299-305.
4. Bossola, M. Pacelli, F., Doglietto, G. B. "Novel treatments for cancer cachexia". Expert Opinion Investigating Drugs 16.8 (2007): 1241-1253.
5. Suzuki, H, A. Asakawa, H. Amitani, N. Nakamura and A. Inui. "Cancer cachexia pathophysiology and management" Journal of Gastroenterology 48.5 (2013): 574-594.
6. Ronga, I., F. Gallucci, F. Riccardi, G. Uomo. "Anorexia-cachexia syndrove in pancreatic cancer: recent advances and new pharmacological approach" 59.1 Advances in Medical Sciences (2014): 1-6.
7. Gorter, R. W. "Cancer Cachexia and Cannabinoids" Research in Complementary Medicine (1999): 021-022.
8. Felder, C. C. and M. Glass. "Cannabinoid receptors and their endogenous agonists" Annual Review of Pharmacology and Toxicology 38.1 (1998): 179-200.
9. Mikuriya, T. H. "Marijuana in medicine: past, present and future." California Medicine 110.1 (1969):34.
10. Aquino, G. and D. Geffen. "Medical Marijuana: A Legitimate Appetite Stimulant?" Nutrition Bytes 10.1 (2005): 1-5.
11. Kirkham, T. C. and C. M. Williams. "Endogenous cannabinoids and appetite" Nutrition Research Reviews 14 (2001): 65-86.
12. Ghosh, P. and S. K. Bhattacharya. "Anticonvulsant action of cannabis in the rat: Role of brain monoamines" Psychopharmacology 59.3 (1978): 293-297.

What is claimed is:

1. A method for treating cachexia and eating disorders in humans and veterinary animals comprising administering to a patient in need thereof a composition comprising:
   (i) cyproheptadine (CYP), wherein the CYP has a maximum dosage of about 0.2 mg/day for each kg of the patient body weight; and (ii) a cannabis compound selected from the group of cannabidiol (CBD) and mixtures of CBD and up to 50% tetrahydrocannabinol (THC).
2. The method of claim 1 wherein the cannabis compound is phytocannabinoids.
3. The method of claim 1 wherein CBD is synthetic CBD.
4. The method of claim 1 wherein THC is synthetic THC.
5. The method of claim 2 wherein the phytocannabinoids are compounded using heated gas or supercritical or subcritical CO2.
6. The method of claim 2 wherein the phytocannabinoids are derived from Cannabis sativa, indica, or hemp.
7. The method of claim 2 wherein CBD also contains minor or trace amounts of cannabinol (CBN), cannabichromene (CBC), cannabigerol (CBG), terpenoids, flavonoids, and other material found in Cannabis plants.
8. The method of claim 1 wherein the dosage of cannabis compound is from about 10 to about 300 mg/day.
9. The method of claim 1 wherein the dosage of CYP to cannabis compound is in the ratio of about 1:50 up to about 1:1500.
10. A composition comprising: (i) cyproheptadine (CYP), wherein the CYP has a maximum dosage of about 0.2 mg/day for each kg of the patient body weight; and (ii) a cannabis compound selected from the group of cannabidiol (CBD) and mixtures of CBD and up to 50% tetrahydrocannabinol (THC).
11. The composition of claim 10 wherein the cannabis compound is phytocannabinoids.
12. The composition of claim 10 wherein CBD is synthetic CBD.
13. The composition of claim 10 wherein THC is synthetic THC.
14. The composition of claim 11 wherein the phytocannabinoids are compounded using heated gas or supercritical or subcritical CO2.

15. The composition of claim 11 wherein the phytocannabinoids are derived from Cannabis sativa, indica, or hemp.

16. The composition of claim 11 wherein CBD also contains minor or trace amounts of cannabinol (CBN), cannabichromene (CBC), cannabigerol (CBG), terpenoids, flavonoids and other material found in Cannabis plants.

17. The composition of claim 10 wherein the amount of cannabis compound present is from about 10 to about 300 mg/day.

18. The composition of claim 10 wherein the ratio of CYP to cannabis compound is about 1:50 up to about 1:1500.

* * * * *